(12) United States Patent
Raymond et al.

(10) Patent No.: US 9,656,094 B2
(45) Date of Patent: *May 23, 2017

(54) BIPHASIC OR MULTIPHASIC PULSE GENERATOR AND METHOD

(71) Applicant: CardioThrive, Inc., Concord, CA (US)

(72) Inventors: Douglas M. Raymond, Livermore, CA (US); Peter D. Gray, Vallejo, CA (US); Walter T. Savage, Concord, CA (US); Shelley J. Savage, Concord, CA (US)

(73) Assignee: CARDIOTHRIVE, INC., Concord, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/661,949

(22) Filed: Mar. 18, 2015

(65) Prior Publication Data

US 2016/0206893 A1   Jul. 21, 2016

Related U.S. Application Data

(63) Continuation-in-part of application No. 14/303,541, filed on Jun. 12, 2014, now Pat. No. 9,616,243.
(Continued)

(51) Int. Cl.
*A61N 1/32* (2006.01)
*A61N 1/39* (2006.01)
(Continued)

(52) U.S. Cl.
CPC ............ *A61N 1/3912* (2013.01); *A61N 1/36* (2013.01); *A61N 1/36128* (2013.01);
(Continued)

(58) Field of Classification Search
CPC .. A61N 1/36; A61N 1/36128; A61N 1/36146; A61N 1/39; A61N 1/3906; A61N 1/3975; A61N 1/3912; A61N 1/3625
(Continued)

(56) References Cited

U.S. PATENT DOCUMENTS

| 4,441,498 A | 4/1984 | Nordling |
| 5,199,429 A | 4/1993 | Kroll et al. |

(Continued)

FOREIGN PATENT DOCUMENTS

| DE | 10 2006 02586 | 12/2007 |
| EP | 1 834 622 | 9/2007 |

(Continued)

OTHER PUBLICATIONS

Yamanouchi, Yoshio et al. "Optimal Small-Capacitor Biphasic Waveform for External Defibrillation: Influence of Phase-1 Tilt and Phase-2 Voltage." Jul. 30, 1998. Journal of the American Heart Association. vol. 98. pp. 2487-2493.*

(Continued)

*Primary Examiner* — Michael Carey
(74) *Attorney, Agent, or Firm* — DLA Piper LLP (US)

(57) ABSTRACT

A dynamically adjustable biphasic or multiphasic pulse generation system and method are provided. The dynamically adjustable biphasic or multiphasic pulse generator system may be used as a pulse generation system for a defibrillator or other type of electrical stimulation medical device.

51 Claims, 11 Drawing Sheets

Related U.S. Application Data

(60) Provisional application No. 61/835,443, filed on Jun. 14, 2013.

(51) Int. Cl.
*A61N 1/36* (2006.01)
*A61N 1/362* (2006.01)

(52) U.S. Cl.
CPC ............ *A61N 1/36146* (2013.01); *A61N 1/39* (2013.01); *A61N 1/3906* (2013.01); *A61N 1/3975* (2013.01); *A61N 1/3625* (2013.01)

(58) Field of Classification Search
USPC ................................ 607/5, 9, 26, 70, 72, 74
See application file for complete search history.

(56) References Cited

U.S. PATENT DOCUMENTS

| | | | |
|---|---|---|---|
| 5,240,995 A | 8/1993 | Gyory et al. | |
| 5,290,585 A | 3/1994 | Elton | |
| 5,338,490 A | 8/1994 | Dietz et al. | |
| 5,362,420 A | 11/1994 | Itoh et al. | |
| 5,402,884 A | 4/1995 | Gilman et al. | |
| 5,489,624 A | 2/1996 | Kantner et al. | |
| 5,536,768 A | 7/1996 | Kantner et al. | |
| 5,573,668 A | 11/1996 | Grosh et al. | |
| 5,643,252 A | 7/1997 | Waner et al. | |
| 5,658,316 A | 8/1997 | Lamond et al. | |
| 5,660,178 A | 8/1997 | Kantner et al. | |
| 5,733,310 A | 3/1998 | Lopin et al. | |
| 5,800,685 A | 9/1998 | Perrault | |
| 5,871,505 A | 2/1999 | Adams | |
| 5,987,354 A | 11/1999 | Cooper | |
| 6,006,131 A | 12/1999 | Cooper et al. | |
| 6,056,738 A | 5/2000 | Marchitto et al. | |
| 6,141,584 A | 10/2000 | Rockwell et al. | |
| 6,197,324 B1 | 3/2001 | Crittenden | |
| 6,251,100 B1 | 6/2001 | Flock et al. | |
| 6,256,533 B1 | 7/2001 | Yuzhakov et al. | |
| 6,266,563 B1 | 7/2001 | Kenknight et al. | |
| 6,315,722 B1 | 11/2001 | Yaegashi | |
| 6,329,488 B1 | 12/2001 | Terry et al. | |
| 6,379,324 B1 | 4/2002 | Gartstein et al. | |
| 6,477,413 B1 | 11/2002 | Sullivan et al. | |
| 6,576,712 B2 | 6/2003 | Feldstein et al. | |
| 6,596,401 B1 | 7/2003 | Terry et al. | |
| 6,597,948 B1 | 7/2003 | Rockwell et al. | |
| 6,611,707 B1 | 8/2003 | Prausnitz et al. | |
| 6,690,959 B2 | 2/2004 | Thompson | |
| 6,714,817 B2 | 3/2004 | Daynes et al. | |
| 6,797,276 B1 | 9/2004 | Glenn et al. | |
| 6,803,420 B2 | 10/2004 | Cleary et al. | |
| 6,908,453 B2 | 6/2005 | Fleming et al. | |
| 6,908,681 B2 | 6/2005 | Terry et al. | |
| 6,931,277 B1 | 8/2005 | Yuzhakov et al. | |
| 7,072,712 B2 | 7/2006 | Kroll et al. | |
| 7,108,681 B2 | 9/2006 | Gartstein et al. | |
| 7,215,991 B2 | 5/2007 | Besson et al. | |
| 7,226,439 B2 | 6/2007 | Prausnitz et al. | |
| 7,463,917 B2 | 12/2008 | Martinez | |
| 7,645,263 B2 | 1/2010 | Angel et al. | |
| 7,797,044 B2 | 9/2010 | Covey et al. | |
| 8,024,037 B2 | 9/2011 | Kumar | |
| 8,527,044 B2 | 9/2013 | Edwards et al. | |
| 8,558,499 B2 | 10/2013 | Ozaki et al. | |
| 8,781,576 B2 | 7/2014 | Savage et al. | |
| 9,089,718 B2 | 7/2015 | Owen et al. | |
| 2001/0031992 A1 | 10/2001 | Fishler et al. | |
| 2002/0016562 A1 | 2/2002 | Cormier et al. | |
| 2002/0045907 A1 | 4/2002 | Sherman et al. | |
| 2002/0082644 A1 | 6/2002 | Picardo et al. | |
| 2003/0017743 A1 | 1/2003 | Picardo et al. | |
| 2003/0055460 A1 | 3/2003 | Owen et al. | |
| 2003/0088279 A1 | 5/2003 | Rissmann et al. | |
| 2003/0167075 A1 | 9/2003 | Fincke | |
| 2003/0197487 A1 | 10/2003 | Tamura et al. | |
| 2004/0105834 A1 | 6/2004 | Singh et al. | |
| 2004/0143297 A1 | 7/2004 | Ramsey, III | |
| 2004/0166147 A1 | 8/2004 | Lundy et al. | |
| 2004/0247655 A1 | 12/2004 | Asmus et al. | |
| 2005/0055460 A1 | 3/2005 | Johnson et al. | |
| 2005/0123565 A1 | 6/2005 | Subramony et al. | |
| 2006/0136000 A1 | 6/2006 | Bowers | |
| 2006/0142806 A1 | 6/2006 | Katzman et al. | |
| 2006/0173493 A1 | 8/2006 | Armstrong et al. | |
| 2006/0206152 A1 | 9/2006 | Covey et al. | |
| 2007/0016268 A1 | 1/2007 | Carter et al. | |
| 2007/0078376 A1 | 4/2007 | Smith | |
| 2007/0143297 A1 | 6/2007 | Recio et al. | |
| 2007/0150008 A1 | 6/2007 | Jones et al. | |
| 2007/0191901 A1 | 8/2007 | Schecter | |
| 2008/0082153 A1 | 4/2008 | Gadsby et al. | |
| 2008/0097546 A1 | 4/2008 | Powers et al. | |
| 2008/0154110 A1 | 6/2008 | Burnes et al. | |
| 2008/0154178 A1 | 6/2008 | Carter et al. | |
| 2008/0177342 A1 | 7/2008 | Snyder | |
| 2008/0312579 A1 | 12/2008 | Chang et al. | |
| 2008/0312709 A1 | 12/2008 | Volpe et al. | |
| 2009/0076366 A1 | 3/2009 | Palti | |
| 2009/0210022 A1* | 8/2009 | Powers ................ A61N 1/3906 607/5 |
| 2009/0318988 A1 | 12/2009 | Powers | |
| 2009/0326400 A1 | 12/2009 | Huldt | |
| 2010/0063559 A1 | 3/2010 | McIntyre et al. | |
| 2010/0160712 A1 | 6/2010 | Burnett et al. | |
| 2010/0241181 A1 | 9/2010 | Savage et al. | |
| 2011/0028859 A1 | 2/2011 | Chian | |
| 2011/0071611 A1 | 3/2011 | Khuon et al. | |
| 2011/0208029 A1 | 8/2011 | Joucla et al. | |
| 2011/0237922 A1 | 9/2011 | Parker, III et al. | |
| 2011/0288604 A1 | 11/2011 | Kaib et al. | |
| 2011/0301683 A1 | 12/2011 | Axelgaard | |
| 2012/0101396 A1 | 4/2012 | Solosko et al. | |
| 2012/0112903 A1 | 5/2012 | Kaib et al. | |
| 2012/0136233 A1 | 5/2012 | Yamashita | |
| 2012/0158075 A1 | 6/2012 | Kaib et al. | |
| 2012/0203297 A1 | 8/2012 | Efimov et al. | |
| 2012/0259382 A1 | 10/2012 | Trier et al. | |
| 2013/0018251 A1 | 1/2013 | Caprio et al. | |
| 2013/0144365 A1 | 6/2013 | Kipke et al. | |
| 2014/0005736 A1 | 1/2014 | Geheb | |
| 2014/0221766 A1 | 8/2014 | Kinast | |
| 2014/0276183 A1 | 9/2014 | Badower | |
| 2014/0277226 A1 | 9/2014 | Poore et al. | |
| 2014/0317914 A1 | 10/2014 | Shaker | |
| 2014/0371566 A1 | 12/2014 | Raymond et al. | |
| 2014/0371567 A1 | 12/2014 | Raymond et al. | |
| 2014/0371805 A1* | 12/2014 | Raymond ............ A61N 1/3912 607/5 |
| 2014/0371806 A1 | 12/2014 | Raymond et al. | |
| 2015/0297104 A1 | 10/2015 | Chen et al. | |
| 2015/0327781 A1 | 11/2015 | Hernandez-Silveira et al. | |

FOREIGN PATENT DOCUMENTS

| | | |
|---|---|---|
| JP | 2005-144164 | 6/2005 |
| JP | 2008-302254 | 12/2008 |
| JP | 2012-135457 | 7/2012 |
| JP | 2012-529954 | 11/2012 |
| WO | WO 03/020362 | 3/2003 |
| WO | WO2010146492 | 12/2010 |

OTHER PUBLICATIONS

U.S. Appl. No. 14/303,541 Claims as of Apr. 4, 2016.*
Yamanouchi, Yoshio, et al. "Optimal Small-Capacitor Biphasic Waveform for External Defibrillation: Influence of Phase-1 Tilt and Phase-2 Voltage." Jul. 30, 1998. Journal of the American Heart Association. vol. 98. pp. 2487-2493.*
PCT International Preliminary Report on Patentability of PCT/US2010/027346 dated Sep. 20, 2011 (12 pages).

(56) References Cited

OTHER PUBLICATIONS

PCT International Search Report of PCT/US10/27346; dated Oct. 14, 2010 (4 pgs.).
PCT Written Opinion of the International Searching Authority of PCT/US10/27346; dated Oct. 14, 2010 (7 pgs.).
PCT International Preliminary Report on Patentability of PCT/US12/65712; dated Jun. 10, 2014 (6 pgs.).
PCT International Search Report of PCT/US2012/065712, dated Mar. 29, 2013 (2 pages).
PCT International Search Report of PCT/US14/42355; dated Nov. 3, 2010 (2 pgs.).
PCT Written Opinion of PCT/US2012/065712, dated Mar. 29, 2013 (5 pages).
PCT Written Opinion of the International Searching Authority of PCT/US14/42355; dated Nov. 3, 2014 (6 pgs.).
PCT International Search Report of PCT/US14/42356; dated Nov. 3, 2010 (2 pgs.).
PCT Written Opinion of the International Searching Authority of PCT/US14/42356; dated Nov. 3, 2014 (6 pgs.).
PCT International Search Report of PCT/US14/42360; dated Nov. 4, 2010 (2 pgs.).
PCT Written Opinion of the International Searching Authority of PCT/US14/42360; dated Nov. 4, 2014 (4 pgs.).
PCT International Search Report of PCT/US14/42409; dated Nov. 4, 2010 (2 pgs.).
PCT Written Opinion of the International Searching Authority of PCT/US14/42409; dated Nov. 4, 2014 (4 pgs.).
PCT International Preliminary Report on Patentability and Written Opinion of PCT/EP2007/009879; dated May 19, 2009 (7 pages).
PCT International Search Report of PCT/EP2007/009879; dated Apr. 29, 2008 (3 pages).
PCT International Written Opinion of PCT/EP2007/009879; dated Apr. 29, 2008 (6 pages).
Chinese First Office Action of CN 201080021650.4 (English and Chinese); dated Jul. 24, 2013 (19 pgs.).
Chinese Second Office Action of CN 201080021650.4 (English and Chinese); dated Jan. 16, 2014 (16 pgs.).
Chinese Third Office Action of CN 201080021650.4 (English and Chinese); dated Jun. 17, 2014 (18 pgs.).
Japanese Notification of Reason for Rejection of JP 2012-500855 (English and Japanese); dated Feb. 17, 2014 (3 pgs.).
Extended European Search Report of EP 2408521 dated Jul. 10, 2012 (8 pages).
"Changes in the passive electrical properties of human stratum corneum due electroporation" dated Dec. 7, 1994. By U. Pliquett, R. Langer, and J. C. Weaver (11 pages).
"Electrical properties of the epidermal stratum corneum" dated Aug. 12, 1974. By T. Yamamoto and Y. Yamamoto (8 pages).
"Non-invasive bioimpedance of intact skin• mathematical modeling and experiments" dated May 2, 2010. By U. Birgersson, E. Birgersson, P. Aberg, I. Nicander, and S. Ollmar (19 pages).
Polymer Microneedles for Controlled-Release Drug Delivery dated Dec. 2, 2005. By J-H. Park, M. G. Allen, and M. R. Prausnitz (12 pages).
"Utilizing Characteristic Electrical Properties of the Epidermal Skin Layers to Detect Fake Fingers in Biometric Fingerprint Systems—A Pilot Study" dated Dec. 1, 2004. By O. G. Martinsen, S. Clausen, J. B. Nysaether, and S. Grimnes (4 pages).
"Lack of Pain Associated with Microfabricated Microneedles" dated Oct. 10, 2000. By S. Kaushik, A. H. Hord, D. D. Denson, D. V. McAlliser, S. Smitra, M. G. Allen, and M. R. Prausnitz (3 pages).
"Two Dimensional Metallic Microelectrode Arrays for Extracellular Stimulation and Recording of Neurons" dated 1993. By A. B. Frazier, D. P. O'Brien, and M. G. Allen (6 pages).
"Insertion of microneedles into skin: measurement and prediction of insertion force and needle facture force" dated Dec. 10, 2003. By S. P. Davis, B. J. Landis, Z. H. Adams, M. G. Allen, and M. R. Prausnitz (9 pages).
"Microneedle Insertion Force Reduction Using Vibratory Actuation" dated 2004. By M. Yang and J. D. Zahn (6 pages).

\* cited by examiner

Variable Capacitor or Capacitor Array (Reservoir)

Variable Impedance module

BIPHASIC OR MULTIPHASIC PULSE GENERATOR AND METHOD

PRIORITY CLAIMS/RELATED APPLICATIONS

This application is a continuation in part of and claims priority under 35 USC 120 to pending U.S. patent application Ser. No. 14/303,541, filed on Jun. 12, 2014 and entitled "Dynamically Adjustable Multiphasic Defibrillator Pulse System And Method" (now published as US 2014-0371805 A1) which in turn claims priority under 35 USC 120 and claims the benefit under 35 USC 119(e) to U.S. Provisional Patent Application Ser. No. 61/835,443 filed Jun. 14, 2013 and titled "Dynamically Adjustable Multiphasic Defibrillator Pulse System and Method" (now expired), the entirety of all of which are incorporated herein by reference.

FIELD

The disclosure relates to medical devices and in particular to devices and methods that generate and deliver therapeutic treatment pulses used in medical devices, such as cardioverters and defibrillators, neuro-stimulators, musculo-skeletal stimulators, organ stimulators and nerve stimulators. More specifically the disclosure relates to the generation by such medical devices of a new and innovatively shaped biphasic or multiphasic pulse waveform.

BACKGROUND

It is well known that a signal having a waveform may have a therapeutic benefit when the signal is applied to a patient. For example, the therapeutic benefit to a patient may be a treatment that is provided to the patient. The therapeutic benefit or therapeutic treatment may include stimulation of a part of the body of the patient or treatment of a sudden cardiac arrest of the patient. Existing systems that apply a signal with a waveform to the patient often generate and apply a well-known signal waveform and do not provide much, or any, adjustability or variability of the signal waveform.

In the context of defibrillators or cardioverters, today's manual defibrillators deliver either an older style Monophasic Pulse (a single high energy single polarity pulse) or the now more common Biphasic Pulse (consisting of an initial positive high energy pulse followed by a smaller inverted negative pulse). Today's implantable cardioverter defibrillators (ICDs), automated external defibrillators (AEDs) and wearable cardioverter defibrillators (WCDs) all deliver Biphasic Pulses with various pulse phase lengths, high initial starting pulse amplitude and various pulse slopes. Each manufacturer of a particular defibrillator, for commercial reasons, has their own unique and slightly different exact timing and shape of the biphasic pulse for their devices' pulses, although they are all based off of the standard biphasic waveform design. Multiple clinical studies over the last couple of decades have indicated that use of these variants of the biphasic waveform has greater therapeutic value than the older monophasic waveform does to a patient requiring defibrillation therapy and that these standard biphasic waveforms are efficacious at appreciably lower levels of energy delivery than the original monophasic waveforms, and with a higher rate of resuscitation success on first shock delivery.

Thus, almost all of the current defibrillator products that use a biphasic waveform pulse have a single high-energy reservoir, which, while simple and convenient, results in severe limitation on the range of viable pulse shapes that can be delivered. Specifically, the second (or Negative) phase of the Biphasic waveform is currently characterized by a lower amplitude starting point than the first (or Positive) phase of the Biphasic waveform, as shown in FIG. 4. This is due to the partial draining of the high-energy reservoir during delivery of the initial Positive phase and then, after inverting the polarity of the waveform so that the Negative phase is able to be delivered, there is only the same partially drained amount of energy remaining in the energy reservoir. This lower amplitude starting point constrains and causes the lower initial amplitude of the Negative phase of the waveform. The typical exponential decay discharge is shown by the Positive phase of the waveform shown in FIG. 4.

The standard biphasic pulse waveform has been in common usage in manual defibrillators and in AEDs since the mid-1990s, and still results in energy levels of anywhere from 120 to 200 joules or more being delivered to the patient in order to be efficacious. This results in a very high level of electrical current passing through the patient for a short period of time which can lead to skin and flesh damage in the form of burns at the site of the electrode pads or paddles in addition to the possibility of damage to organs deeper within the patient's body, including the heart itself. The significant amounts of energy used for each shock and the large number of shocks that these AED devices are designed to be able to deliver over their lifespan, has also limited the ability to further shrink the size of the devices.

WCDs generally need to deliver shocks of 150-200 joules in order to be efficacious, and this creates a lower limit on the size of the electrical components and the batteries required, and hence impacts the overall size of the device and the comfort levels for the patient wearing it.

ICDs, given that they are implanted within the body of patients, have to be able to last for as many years as possible before their batteries are exhausted and they have to be surgically replaced with a new unit. Typically ICDs deliver biphasic shocks of up to a maximum of 30-45 joules, lower than is needed for effective external defibrillation as the devices are in direct contact with the heart tissue of the patient. Subcutaneous ICDs, differ slightly in that they are not in direct contact with the heart of the patient, and these generally deliver biphasic shocks of 65-80 joules in order to be efficacious. Even at these lower energy levels there is significant pain caused to the patient if a shock is delivered in error by the device. Most existing devices are designed to last for between 5-10 years before their batteries are depleted and they need to be replaced.

Another, equally common type of defibrillator is the Automated External Defibrillator (AED). Rather than being implanted, the AED is an external device used by a third party to resuscitate a person who has suffered from sudden cardiac arrest. FIG. 9 illustrates a conventional AED 800, which includes a base unit 802 and two pads 804. Sometimes paddles with handles are used instead of the pads 804. The pads 804 are connected to the base unit 802 using electrical cables 806.

A typical protocol for using the AED 800 is as follows. Initially, the person who has suffered from sudden cardiac arrest is placed on the floor. Clothing is removed to reveal the person's chest 808. The pads 804 are applied to appropriate locations on the chest 808, as illustrated in FIG. 9. The electrical system within the base unit 802 generates a high voltage between the two pads 804, which delivers an electrical shock to the person. Ideally, the shock restores a normal cardiac rhythm. In some cases, multiple shocks are required.

DETAILED DESCRIPTION OF ONE OR MORE EMBODIMENTS

Figure 5A:
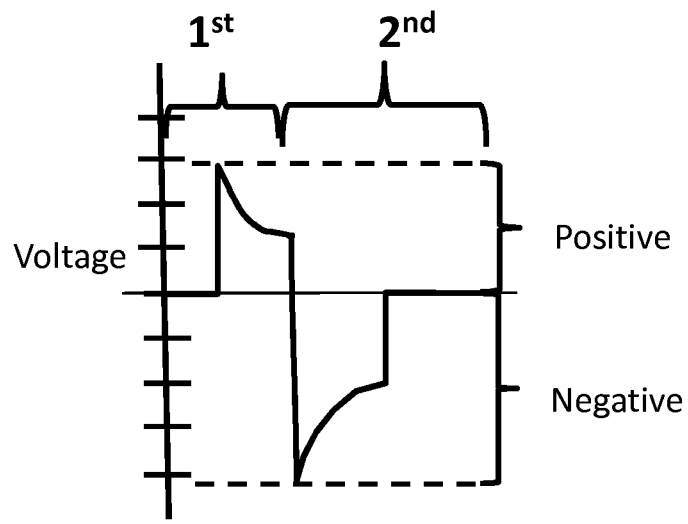
FIGS. 5A, 5B and 5C illustrate different examples of a novel biphasic or multiphasic pulse waveform generated by the biphasic or multiphasic waveform generator where the second (negative) phase of the waveform is larger in amplitude than the amplitude of the first (positive) phase of the waveform.
Figure 5B:
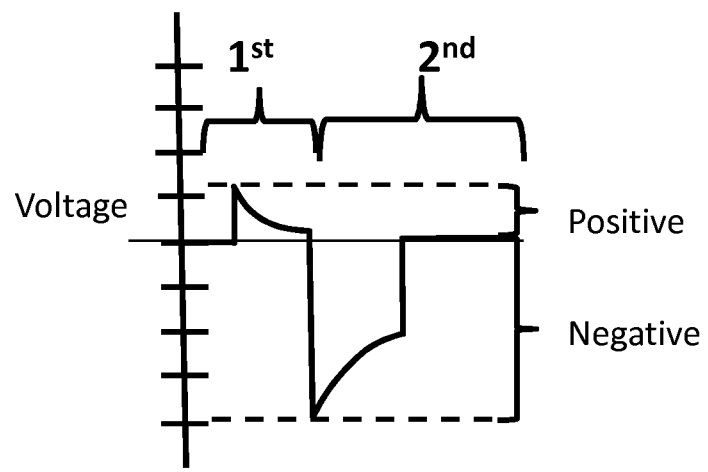
Figure 5C:
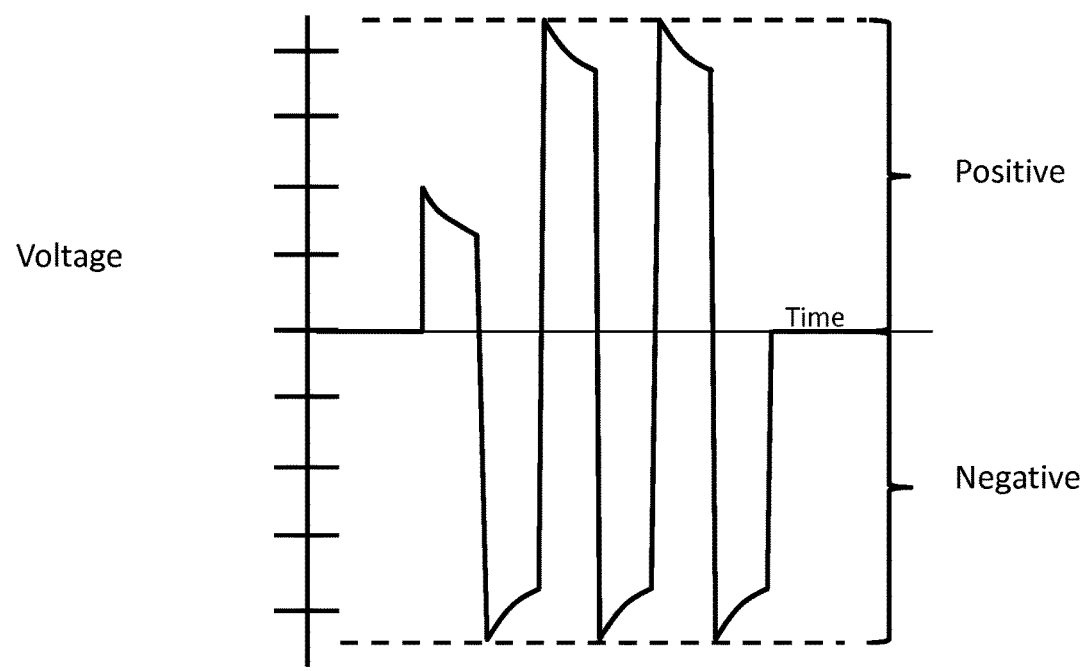

The disclosure is applicable to various medical devices including all defibrillator types: external (manual, semi-automated, and fully automated), wearable, implantable and subcutaneous implantable. In addition to defibrillators, the medical device may also be cardioverters and external/internal pacers, as well as other types of electrical stimulation medical devices, such as: neuro-stimulators, musculoskeletal stimulators, organ stimulators and nerve/peripheral nerve stimulators, whether the devices are external or implantable. The novel biphasic or multiphasic waveform generator may be particularly useful for any type of defibrillator and examples of the novel biphasic or multiphasic waveform generator system will be described in the context of a defibrillator for illustration purposes. It will be appreciated, however, that the novel biphasic or multiphasic waveform generator may generate and deliver a much wider range of waveforms than has previously been possible in the art (or as shown in the examples) including a new generation/family of novel biphasic or multiphasic waveforms, as shown in FIG. 5A, FIG. 5B and FIG. 5C. Thus, the novel biphasic or multiphasic waveform generator has greater utility to existing devices since it may be used to generate one or more of this family of novel lower energy biphasic pulses. For example, the novel biphasic or multiphasic waveform generator may be configured to generate and deliver a wide range of the new low energy biphasic or multiphasic waveforms with varying pulse timings, phase tilts and amplitudes. Such waveforms can be used in the various medical devices described above. In these devices the pulse generator system may be used to generate therapeutic treatment pulses and then provide the pulses to a patient using paddles or pads or other suitable forms of electrodes.

The novel biphasic or multiphasic waveform generator can be embodied in a number of different ways, constituting a range of different potential circuit designs all of which are within the scope of this disclosure since any of the circuit designs would be able to generate and deliver a wide range of biphasic and/or multiphasic waveforms including the new family/generation of low energy biphasic and/or multiphasic waveforms where the first phase of the waveform has a lower amplitude than the second phase of the waveform.

Figure 1:
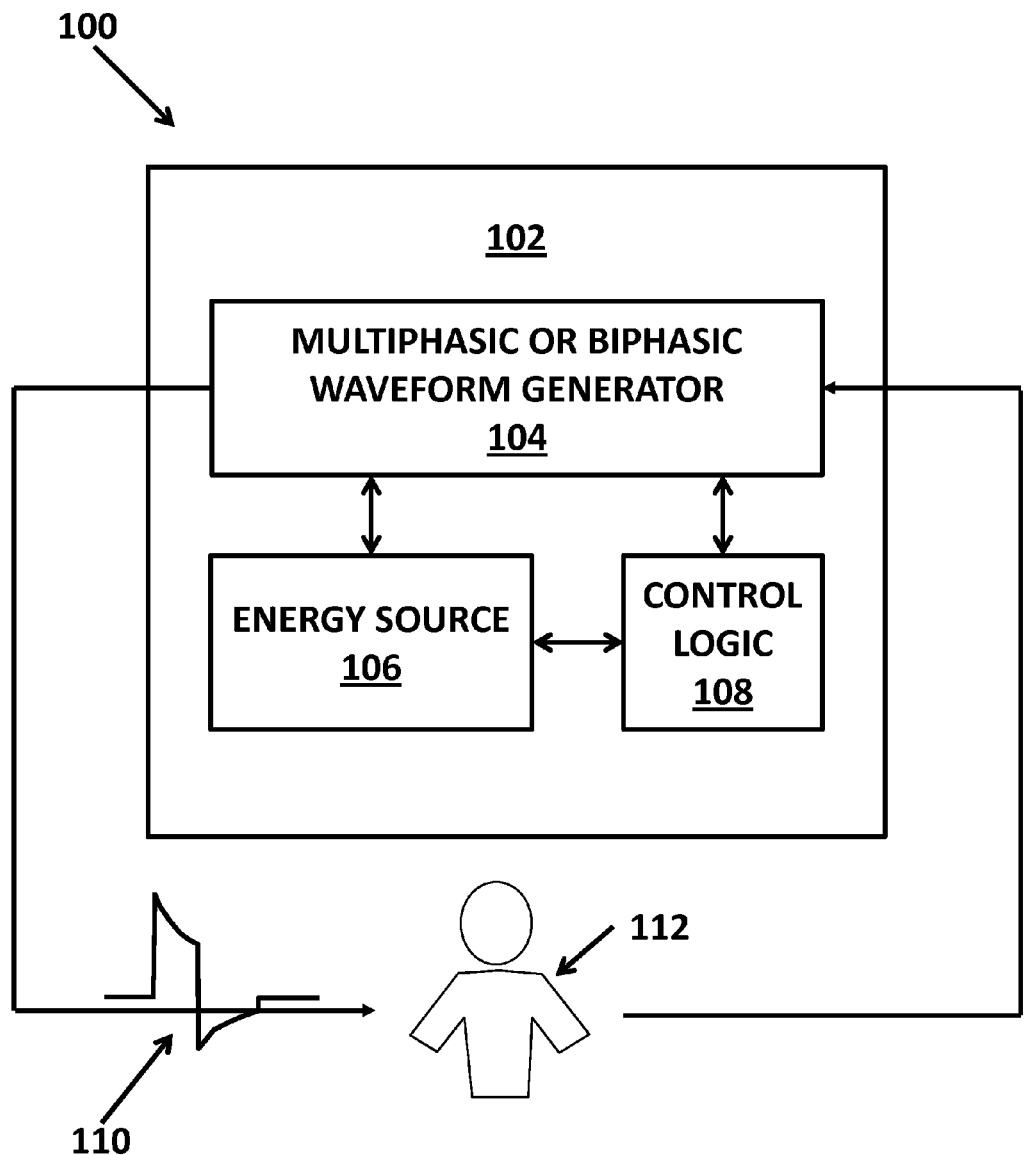
FIG. 1 illustrates a medical device having a biphasic or multiphasic waveform generator.

FIG. 1 illustrates a medical device system 100 having a novel biphasic or multiphasic waveform generator 104. As described above, the medical device system may be any type of defibrillator system or any of the other types of medical devices described above. The medical device system 100 may include a medical device 102 that generates and delivers a novel biphasic or multiphasic pulse waveform 110 to a patient 112. The novel biphasic or multiphasic pulse waveform 110 may be a therapeutic pulse, a defibrillation pulse and the like. As shown in FIG. 1, the medical device 102 may include a novel multiphasic or biphasic waveform generator 104, an energy source 106 and a control logic 108. The novel multiphasic or biphasic waveform generator 104 may generate a novel biphasic or multiphasic pulse waveform 110 using the energy stored/generated by the energy source 106.

The novel biphasic or multiphasic pulse waveform 110 may have one or more first phases and one or more second phases wherein the first and second phases may be opposite polarities. In one biphasic waveform example, the first phase may be a positive phase, the second phase may be a negative phase and the second phase of the waveform may be larger in amplitude than the amplitude of the first phase of the waveform as shown in FIGS. 5A and 5B. Further, as shown in FIG. 5C, a novel multiphasic pulse waveform that may be generated by the multiphasic or biphasic waveform generator 104 is shown in which the biphasic or multiphasic pulse waveform 110 has more than one first phases and more than one second phases of the pulse waveform. In the example in FIG. 5C, each first phase has a positive polarity and each second phase has a negative polarity. For example, the amplitude of the second phase may be less than 2500 volts and the first phase would be smaller than the second phase. The multiphasic or biphasic waveform generator 104 may deliver an energy of between 0.1 to 200 joules of energy to a patient during the first phase and second phase of the generated pulse waveform and an inter-pulse period between the first and second phases. The multiphasic or biphasic waveform generator 104 may deliver the waveform to the patient during a 2 ms to 20 ms time period.

The control logic unit 108 may be coupled to and/or electrically connected to the multiphasic or biphasic waveform generator 104 and the energy source 106 to control each of those components to generate various version of the biphasic or multiphasic pulse waveform 110. The energy source 106 may be one or more power sources and one or more energy reservoirs. The control logic unit 108 may be implemented in hardware. For example, the control logic unit 108 may be a plurality of lines of computer code that may be executed by a processor that is part of the medical device. The plurality of lines of computer code may be executed by the processor so that the processor is configured to control the multiphasic or biphasic waveform generator 104 and the energy source 106 to generate the biphasic or multiphasic pulse waveform 110. In another embodiment, the control logic unit 108 may be a programmable logic device, application specific integrated circuit, a state machine, a microcontroller that then controls the multiphasic or biphasic waveform generator 104 and the energy source 106 to generate the biphasic or multiphasic pulse waveform 110. The control logic unit may also include analog or digital switching circuitry when the high voltage switching component 109 is part of the control logic unit 108.

As shown in FIG. 1, the biphasic or multiphasic pulse waveform 110 may be delivered to the patient 112 using one or more patient contact devices. The one or more patient contact devices may be, for example, an electrode, a wire, a paddle, a pad or anything else that is capable of delivering the biphasic or multiphasic pulse waveform 110 to the patient 112. To further illustrate a medical device that has the multiphasic or biphasic waveform generator 104 and the energy source 106, an example of a defibrillator that has the multiphasic or biphasic waveform generator 104 and the energy source 106 is now described in further detail.

Figure 2:
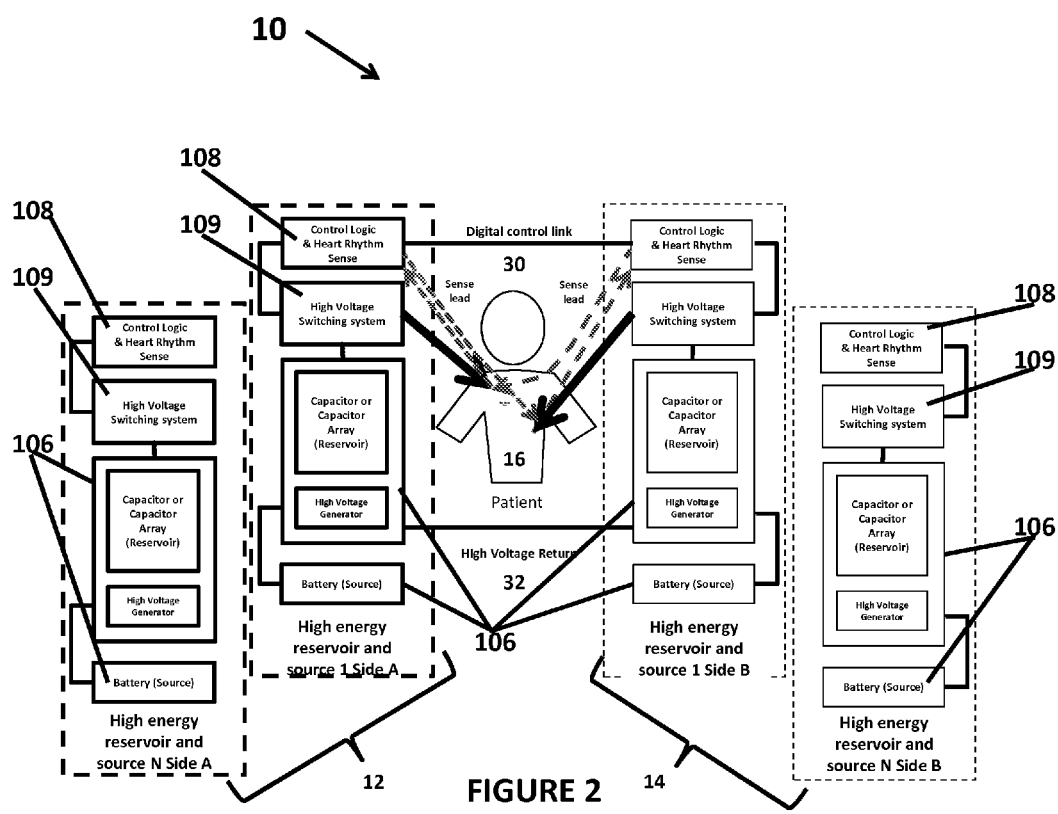
FIG. 2 illustrates a defibrillator medical device with a multiphasic waveform generator with a plurality of independent subsystems each with its own energy reservoir and energy source.
Figure 3:
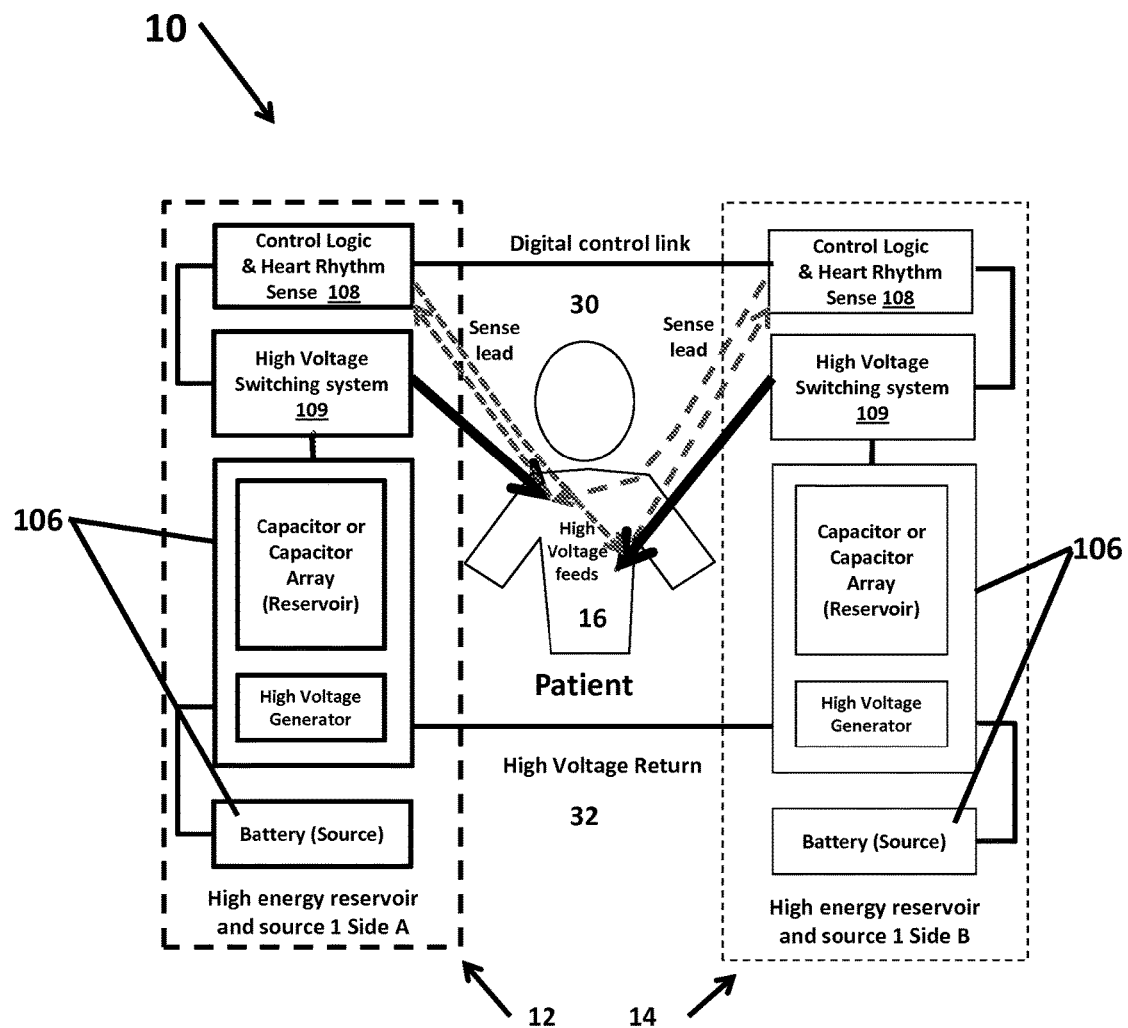
FIG. 3 illustrates a defibrillator medical device with a biphasic waveform generator with two independent subsystems each with its own energy reservoir and energy source.
Figure 4:
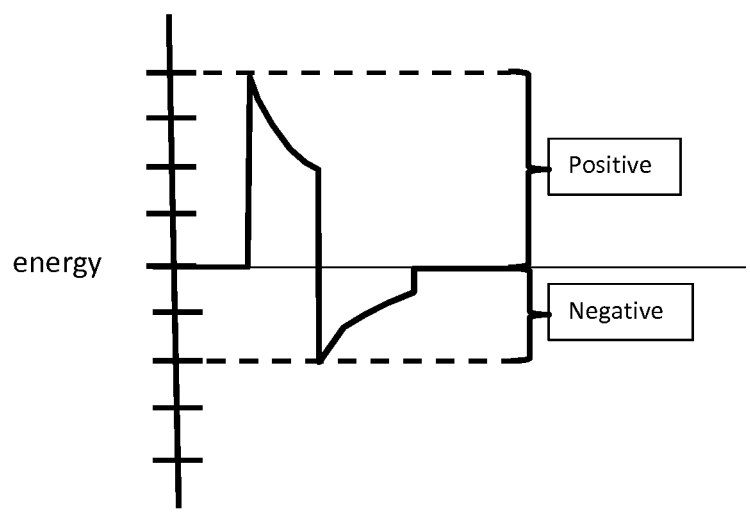
FIG. 4 illustrates a standard biphasic pulse waveform where the second (negative) phase of the waveform is smaller in amplitude than that of the first (positive) phase of the waveform.

FIG. 2 illustrates a defibrillator medical device 10 with a multiphasic waveform generator with a plurality of independent subsystems each with its own energy reservoir and energy source and FIG. 3 illustrates a defibrillator medical device 10 with a biphasic waveform generator with two independent subsystems each with its own energy reservoir and energy source. In an embodiment of the novel multiphasic or biphasic waveform generator 104 and the energy source 106, the components may use two or more physically and electrically distinct subsytems 12, 14 in which each subsystem has the waveform generator 104, the energy source 106 and the control logic 108 as shown in FIGS. 2-3. The reservoirs of stored electrical energy may be in two or more different circuits (see FIG. 2 and FIG. 3) that function together in a coordinated fashion in order to generate and deliver the pulse waveform where each phase of the waveform is produced from a separate reservoir of the stored energy. The reservoirs of energy may be of the same size/quantity or else of widely different sizes and may be supplied by one or more energy sources.

The energy source 106 is not limited to any particular number of energy reservoirs (such as capacitors) or energy sources (such as batteries). Thus, the medical device system 10 may have a plurality or "n" number (as many as wanted) of subsystems 12, 14 that together can be utilized to generate the various multiphasic or biphasic waveforms. In the example embodiments shown in FIG. 2 and FIG. 3, there may be two sides, such as side A and side B as shown, and each side may have one or more of the subsystems 12, 14 and each subsystem may generate a phase of the pulse waveform to generate the biphasic or multiphasic waveform with one or more first phases and one or more second phases. The two or more subsystems 12, 14 permit the system to shape the various characteristics of first and second phases separately from each other. For example, in one example, the first phase may have a positive polarity and its characteristics may be shaped independently of the second phase that may have a negative polarity and its characteristics. The above described functions may be accomplished through the use of a fast switching high-energy/voltage switch system as described below. The fast switching high-energy/voltage switch system 109 may be part of the control logic unit 108 or the generator 104.

Each subsystem 12, 14 of each side, as shown in FIG. 2 and FIG. 3, may have the control logic and heart rhythm sense component 108 (that is connected to a similar component on the other side by a digital control link 30 as shown in FIG. 2 and FIG. 3) that may be also coupled to a high voltage switching system component 109. The high voltage switching system component 109 may be implemented using either analog circuits or digital circuits or even some hybrid of the two approaches. Furthermore, the high voltage switching system component 109 may be implemented through the use of mechanical or solid-state switches or a combination of the two. The energy reservoir may also be coupled, by a high voltage return line 32 to the other side of the system as shown in FIG. 2 and FIG. 3. The high voltage return 32 electrically completes the circuit and is present in existing defibrillators, but in a slightly different form since in the existing style of devices it is split into two parts in the form of the two leads which go from the main defibrillator device to the internal or external surface of the patient.

Figure 6:
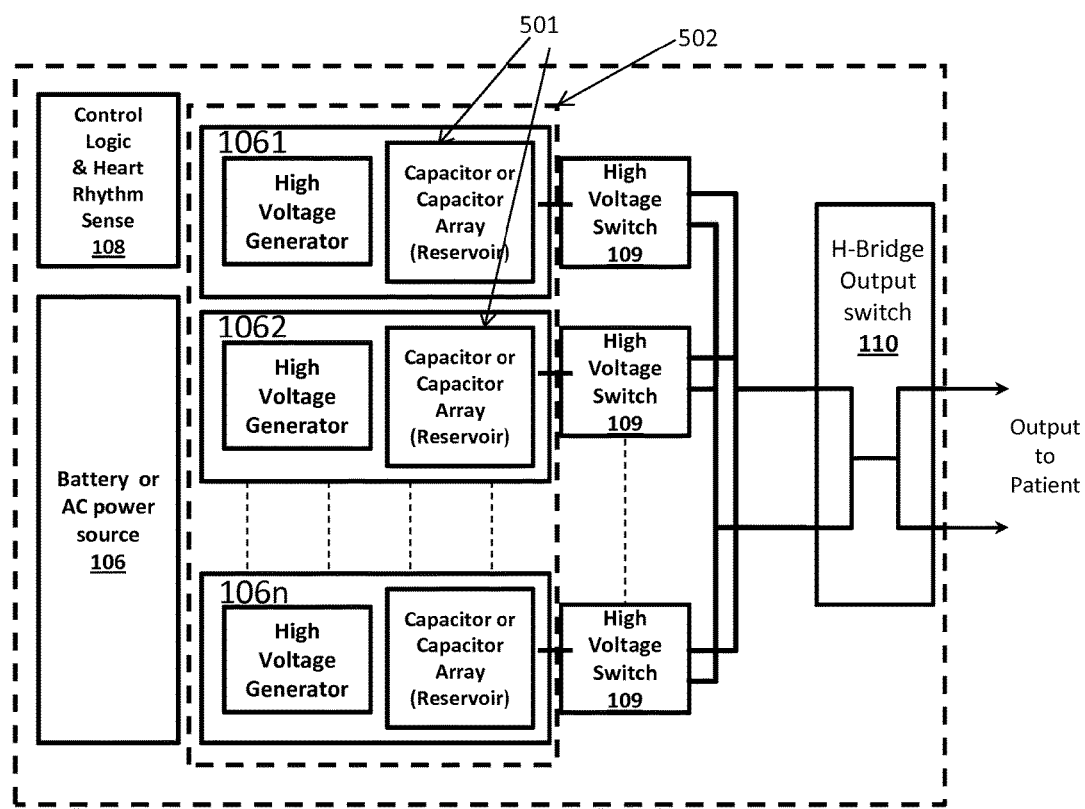
FIG. 6 illustrates an embodiment of a biphasic/multiphasic waveform generator with a single circuit containing multiple energy reservoirs which can be dynamically charged separately from a single energy source and then discharged through the H-bridge.
Figure 7:
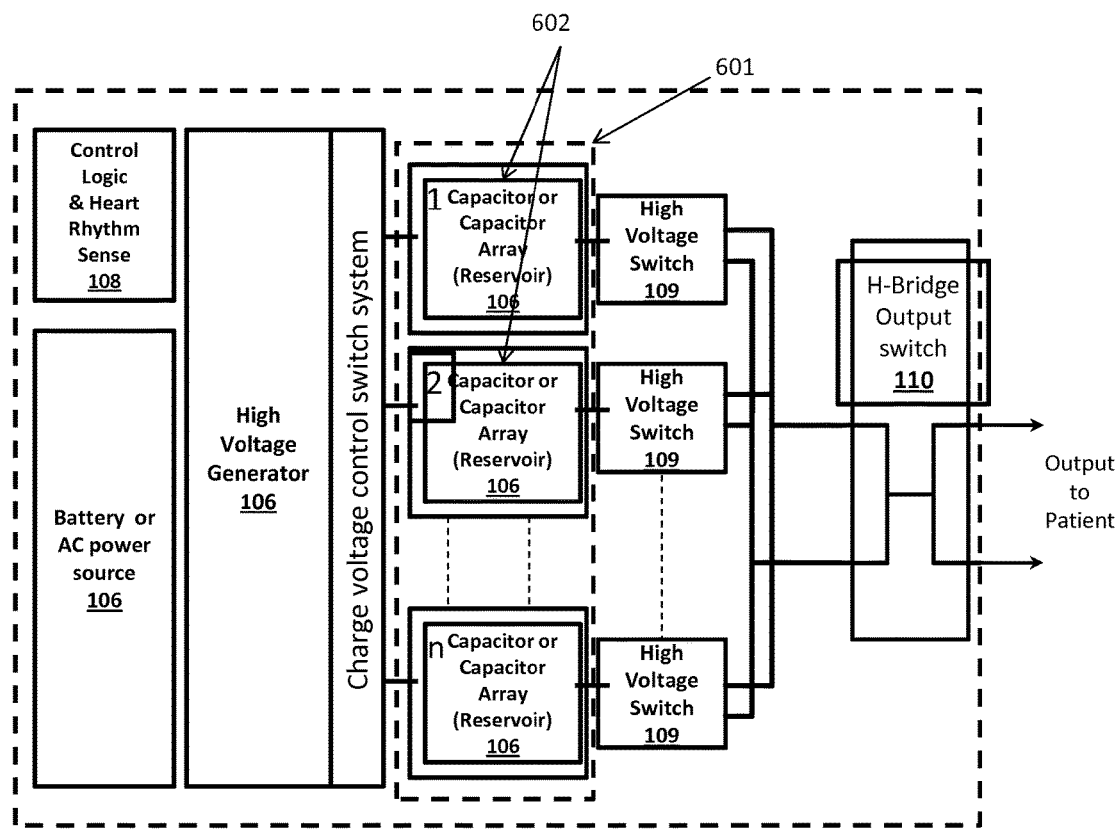
FIG. 7 illustrates a biphasic/multiphasic waveform generator with a single circuit containing multiple energy reservoirs which can be dynamically charged separately and then discharged through an H-bridge.
Figure 8:
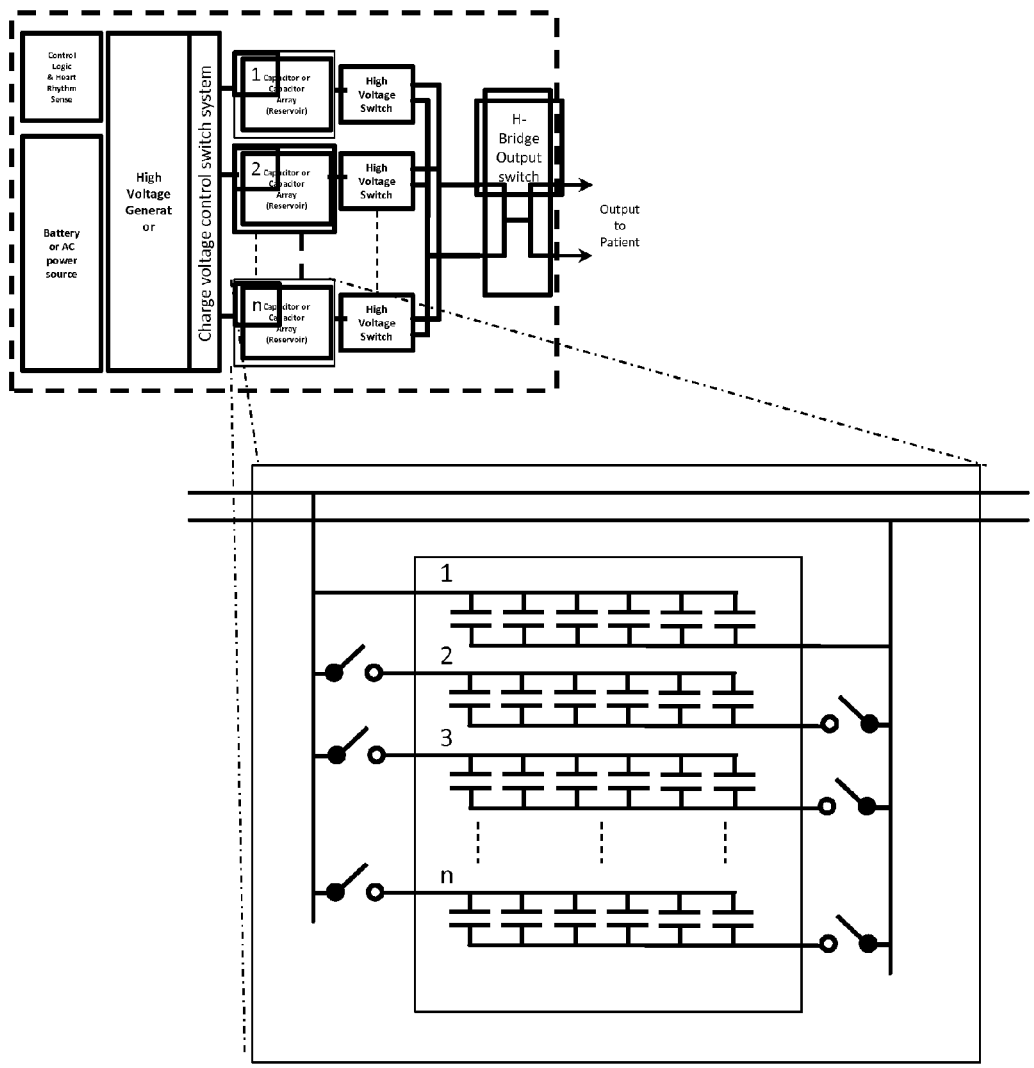
FIG. 8 illustrates a circuit for adjusting the biphasic or multiphasic waveform generator system's capacitance.
Figure 9:
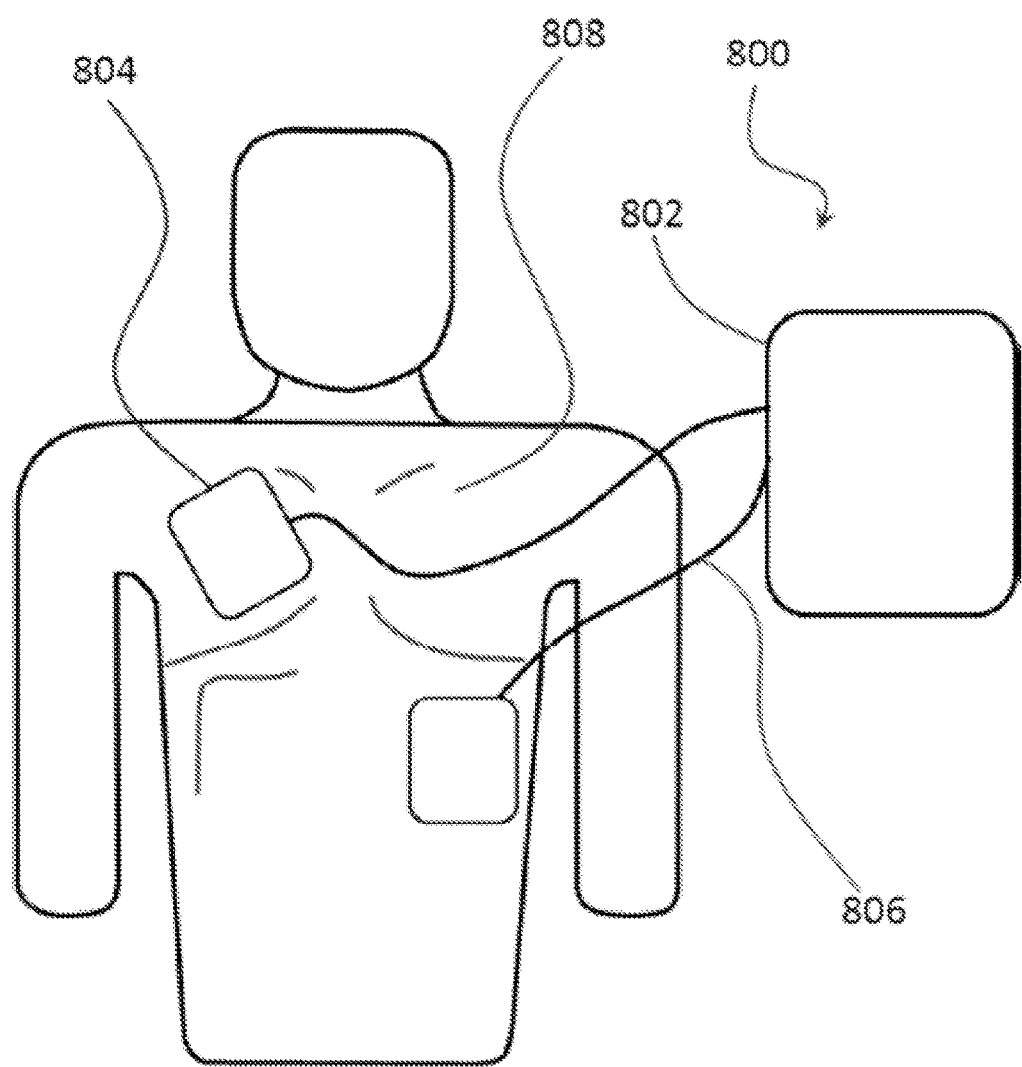
FIG. 9 diagrammatically illustrates an example of a conventional external defibrillator.

FIGS. 5A-5C illustrate examples of the biphasic or multiphasic waveforms that may be generated by the systems shown in FIGS. 2-3 as well as the systems shown in FIGS. 6-8. In the examples in FIGS. 5A-5B a first phase may be a positive polarity and the second phase may be a negative polarity. However, the biphasic or multiphasic waveforms also may have a negative polarity first pulse and a positive polarity second pulse. As shown in FIGS. 5A and 5B, the first phase pulse amplitude may be smaller than the second phase amplitude. FIG. 5C illustrates a multiphasic waveform in which the waveform has two or more positive polarity phases and two or more negative polarity phases.

In another embodiment (see FIG. 6) the system 10 makes use of two or more reservoirs of stored electrical energy 501 (such as high voltage generator and reservoir 1061, high voltage generator and reservoir 1062 and high voltage generator and reservoir 106n) that are either statically or dynamically allocated from within a single circuit 502 and that function together in a coordinated fashion in order to generate and deliver the final waveform where each phase of the waveform is produced from a separate reservoir of the stored energy. The reservoirs of energy 501 may be of the same size/quantity or else of widely different sizes and may be supplied by one or more energy sources. The system 10 may also have the high voltage switch 109 for each reservoir 501 and an H-bridge switch 110 that may be part of the control logic unit 108 or the generator 104. The H-bridge circuit is a known electronic circuit that enables a voltage to be applied across a load, M, in either direction using one or more switches (see http://cp.literature.agilent.com/litweb/pdf/5989-6288EN.pdf that is incorporated by reference herein for additional details about the H-bridge circuit.)

In another embodiment (see FIG. 7) the system makes use of at least one reservoir of stored electrical energy 601 in a configuration that is divided up and either statically or dynamically allocated into two or more portions of stored energy 602 from within a single circuit and that generates and delivers the final waveform in a coordinated fashion where each phase of the waveform is produced from a separate portion of the stored energy. The portions of energy 602 may be of the same size/quantity or else of widely different sizes and may be supplied by the one or more energy sources. Essentially, this involves charging one or more group(s)/array(s) of capacitors (the number of capacitors in a statically or dynamically created group is based on the voltage and energy requirements for the phase of the waveform or waveform that is to be generated and delivered) and then discharging a select number of capacitors in a group that is configured as required to provide the desired waveform or phase of a waveform. The charging and discharging of capacitors in parallel and in series is well known in the art. Through a configuration of switches (mechanical or solid state) one can disconnect a certain number of capacitors from the original group/array of capacitors, thus separating the stored energy into two (or more) portions/reservoirs that feed an H-bridge switch 110, allowing the creation of a wide range of waveform phases with different amplitudes, shapes and timings.

Another embodiment of the system makes use of a direct current generation source in order to generate the initial phase of the waveform and then uses one or more reservoirs of stored electrical energy in order to generate the second phase of the waveform and any additional phases of the waveform. The energy reservoirs used may be supplied by one or more energy sources.

Another embodiment of the system makes use of a direct current generation source in order to generate the initial phase of the waveform and then uses one or more additional direct current generation sources, configured alone, together, or else in combination with reservoirs of stored electrical energy, in order to generate the second phase of the waveform and any additional phases of the waveform. The energy reservoirs used may be supplied by one or more energy sources.

In additional embodiments, the pulse generator may be configured with the circuitry, processors, programming and other control mechanisms necessary to separately and individually vary the phase timings, the inter-phase pulse timing(s), the phase tilts and the phase amplitudes necessary to customize and optimize the waveform for the patient at hand and for the specific therapeutic purpose for which the waveform is being used.

The above described functions may be accomplished through the use of a fast switching high-energy/voltage switch system 109 which can be either analog or digital in nature or even some hybrid of the two approaches as shown in FIG. 2 and FIG. 3. The switching can be accomplished through the use of mechanical or solid-state switches or a combination of the two.

Figure 10:
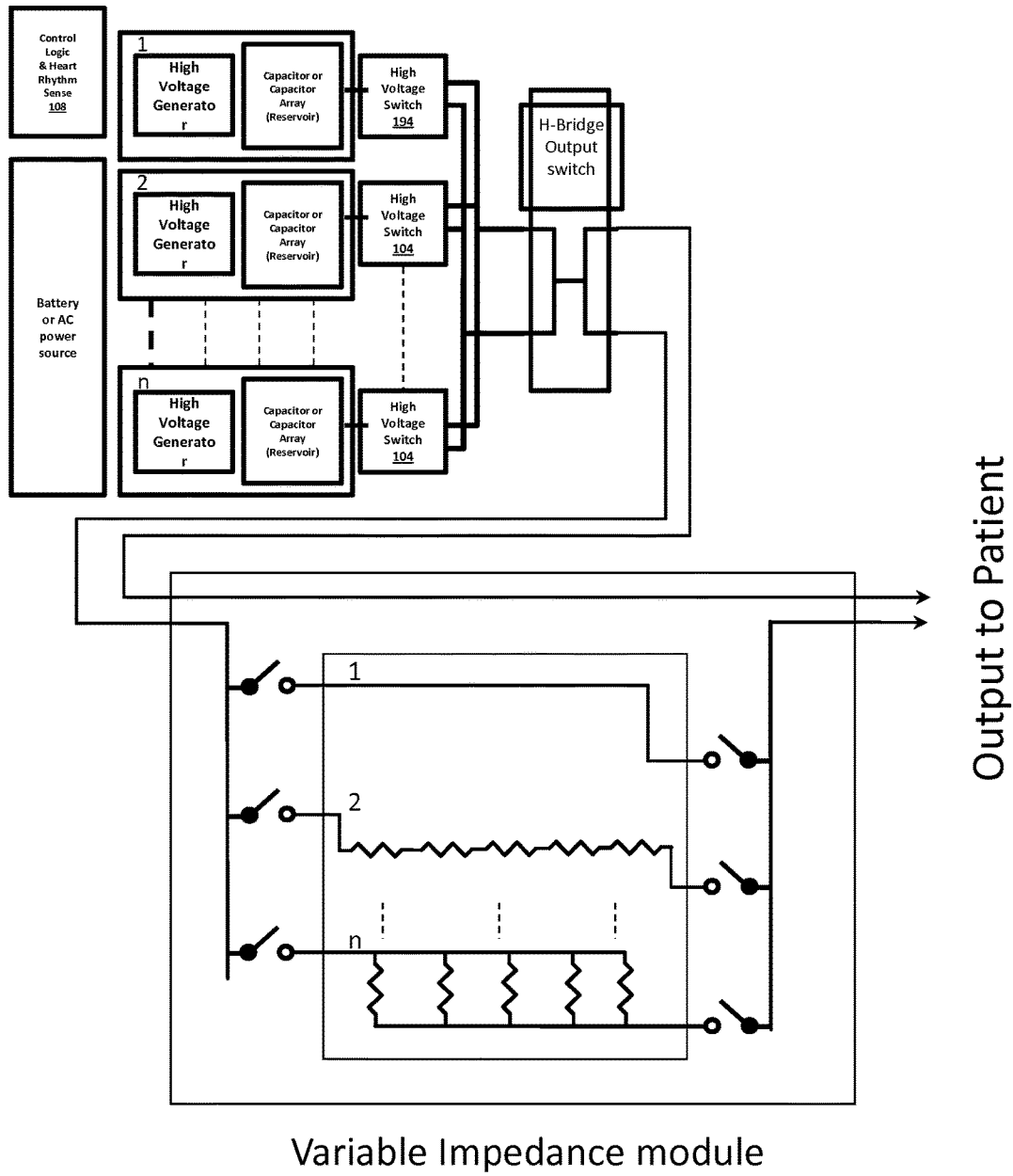
FIG. 10 illustrates a circuit for adjusting the waveform generator system's resistance/impedance.

Other embodiments of the system discharge part of the waveform's initial phase energy through the use of a statically or dynamically allocated group of resistive power splitters (see FIG. 10), which steps the waveform's initial phase amplitude down across the group of resistors, and in this manner delivers a smaller remaining amplitude of the waveform's initial phase to the patient, while still delivering a full amplitude of the second phase (and any additional phases) to the patient.

Many embodiments of the system can make use of one or more additional circuitry modules or subsystems intended to alter the RC constant of the pulse delivery circuitry for one or more of the pulse phases, and hence alter the tilt of the phase of the pulse waveform involved. These modules or subsystems can consist of an array of capacitors or an array of resistors, or of a combination of the two (see FIG. 8 and FIG. 10).

In some embodiments of the system, the system may provide for the recharging of individual energy reservoirs by the energy sources during times (including inter-phase pulse times) that an individual energy reservoir is not selected for discharge. This provides the opportunity to interlace equivalent amplitude initial multiphasic pulses utilizing several different high energy reservoirs.

While the foregoing has been with reference to a particular embodiment of the disclosure, it will be appreciated by those skilled in the art that changes in this embodiment may be made without departing from the principles and spirit of the disclosure, the scope of which is defined by the appended claims.

The invention claimed is:

1. A pulse generator, comprising:
a pulse waveform generator that generates a pulse waveform having at least one first phase of the pulse waveform and at least one second phase of the pulse waveform, wherein the first phase has an amplitude whose value is less than an amplitude of the second phase and wherein the first phase has a polarity and the second phase has an opposite polarity to the first phase;
at least a first subsystem that generates at least the first phase of the pulse waveform, the subsystem having a power source and an energy reservoir;
at least a second subsystem that generates at least the second phase of the pulse waveform, the second subsystem having a second power source and a second energy reservoir; and
a control logic unit that controls the first and second subsystems to generate the pulse waveform having the at least one first phase and the at least one second phase.

2. The generator of claim 1, wherein the control logic unit further comprises a switching component that switches between the first and second subsystems to generate the pulse waveform having the at least one first phase and the at least one second phase.

3. The generator of claim 1, wherein the generated pulse waveform has a plurality of first phases and a plurality of second phases to generate a multiphasic pulse waveform.

4. The generator of claim 1, wherein the generated pulse waveform has a single first phase and a single second phase to generate a biphasic pulse waveform.

5. The generator of claim 1, wherein the generated pulse waveform has the first phase that has a positive polarity and the second phase that has a negative polarity.

6. The generator of claim 1, wherein the generated pulse waveform has the first phase that has a negative polarity and the second phase that has a positive polarity.

7. The generator of claim 1, wherein the generated pulse waveform has an energy of between 0.1 to 200 joules of energy delivered to a patient during the first phase and second phase of the generated pulse waveform and an inter-pulse period between the first and second phases.

8. The generator of claim 7, wherein the energy of the generated pulse waveform is delivered to the patient during a 2 ms to 20 ms time period.

9. The generator of claim 1 further comprising an adjustment component that adjusts a slope of at least one phase of the pulse waveform or an amplitude of at least one phase of the pulse waveform.

10. The generator of claim 9, wherein the adjustment component is an array of capacitors wherein one or more capacitors are selected to adjust a slope of at least one phase of the pulse waveform or an amplitude of at least one phase of the pulse waveform.

11. The generator of claim 10, wherein the array of capacitors is one of capacitors connected in series, capacitors connected in parallel and capacitors connected in series and parallel.

12. The generator of claim 1 further comprising an array of capacitors that adjusts a slope of at least one phase of the pulse waveform.

13. The generator of claim 12, wherein the array of capacitors is one of capacitors connected in series, capacitors connected in parallel and capacitors connected in series and parallel.

14. The generator of claim 9, wherein the adjustment component is an array of resistors wherein one or more resistors are selected to adjust a slope of at least one phase of the pulse waveform or an amplitude of at least one phase of the pulse waveform.

15. The generator of claim 14, wherein the array of resistors is one of resistors connected in series, resistors connected in parallel and resistors connected in series and parallel.

16. The generator of claim 1, wherein the control logic unit adjusts a timing for at least one phase of the pulse waveform.

17. The generator of claim 16, wherein the control logic unit adjusts the timing for at least one phase of the pulse waveform based on a heart rhythm of a patient.

18. The generator of claim 1, wherein the control logic unit adjusts a timing of an inter-phase period between the first phase and the second phase of the pulse waveform.

19. The generator of claim 18, wherein the control logic unit adjusts the timing for the inter-phase period based on a heart rhythm of a patient.

20. A biphasic or multiphasic pulse generator, comprising:
a pulse waveform generator that generates a pulse waveform having at least one first phase of the pulse waveform and at least one second phase of the pulse waveform, wherein the first phase has an amplitude whose value is less than an amplitude of the second phase and wherein the first phase has a polarity and the second phase has an opposite polarity to the first phase;
a first subsystem that generates at least the first phase and the second phase of the pulse waveform, the first subsystem having an array of power sources and an array of energy reservoirs that are capable of being allocated into a first group and a second group in order to separately generate the first and second phases of the pulse waveform using the first and second groups, respectively, of the first subsystem; and
a control logic unit that controls the allocation of the first and second groups from the first subsystem to generate the pulse waveform having the at least one first phase and the at least one second phase.

21. The generator of claim 20, wherein the control logic unit further comprises a switching component that switches between the first group and second group of the first subsystem to generate the pulse waveform having the at least one first phase and the at least one second phase.

22. The generator of claim 20, wherein the generated pulse waveform has a plurality of first phases and a plurality of second phases to generate a multiphasic pulse waveform.

23. The generator of claim 20, wherein the generated pulse waveform has a single first phase and a single second phase to generate a biphasic pulse waveform.

24. The generator of claim 20, wherein the generated pulse waveform has the first phase that has a positive polarity and the second phase that has a negative polarity.

25. The generator of claim 20, wherein the generated pulse waveform has the first phase that has a negative polarity and the second phase that has a positive polarity.

26. The generator of claim 20, wherein the generated pulse waveform has an energy of between 0.1 to 200 joules of energy delivered to a patient during the first phase and second phase of the generated pulse waveform and an inter-pulse period between the first and second phases.

27. The generator of claim 26, wherein the energy of the generated pulse waveform is delivered to the patient during a 2 ms to 20 ms time period.

28. The generator of claim 20 further comprising an adjustment component that adjusts a slope of at least one phase of the pulse waveform or an amplitude of at least one phase of the pulse waveform.

29. The generator of claim 28, wherein the adjustment component is an array of capacitors wherein one or more capacitors are selected to adjust a slope of at least one phase of the pulse waveform or an amplitude of at least one phase of the pulse waveform.

30. The generator of claim 29, wherein the array of capacitors is one of capacitors connected in series, capacitors connected in parallel and capacitors connected in series and parallel.

31. The generator of claim 20 further comprising an array of capacitors that adjusts a slope of at least one phase of the pulse waveform.

32. The generator of claim 31, wherein the array of capacitors is one of capacitors connected in series, capacitors connected in parallel and capacitors connected in series and parallel.

33. The generator of claim 28, wherein the adjustment component is an array of resistors wherein one or more resistors are selected to adjust a slope of at least one phase of the pulse waveform or an amplitude of at least one phase of the pulse waveform.

34. The generator of claim 33, wherein the array of resistors is one of resistors connected in series, resistors connected in parallel and resistors connected in series and parallel.

35. The generator of claim 20, wherein the control logic unit adjusts a timing for at least one phase of the pulse waveform.

36. The generator of claim 35, wherein the control logic unit adjusts the timing for at least one phase of the pulse waveform based on a heart rhythm of a patient.

37. The generator of claim 20, wherein the control logic unit adjusts a timing of an inter-phase period between the first phase and the second phase of the pulse waveform.

38. The generator of claim 37, wherein the control logic unit adjusts the timing for the inter-phase period based on a heart rhythm of a patient.

39. A method for generating a therapeutic pulse waveform, comprising:
generating at least one first phase of a pulse waveform using at least a first subsystem having a power source and an energy reservoir to generate the at least one first phase;
generating at least one second phase of the pulse waveform using at least a second subsystem having a second power source and a second energy reservoir to generate the at least one second phase, wherein the at least one first phase of the pulse waveform is smaller in amplitude than the amplitude of the at least one second phase of the pulse waveform and wherein the first phase has a polarity and the second phase has an opposite polarity to the first phase; and
controlling a selection of the at least one first phase and the at least one second phase to generate the pulse waveform having the at least one first phase and the at least one second phase.

40. The method of claim 39, wherein controlling the selection of the at least one first pulse and the at least one second pulse further comprises switching, using a switching component, between at least one first phase and the at least one second phase to generate the pulse waveform.

41. The method of claim 39, wherein the generated pulse waveform has a plurality of first phases and a plurality of second phases to generate a multiphasic pulse waveform.

42. The method of claim 39, wherein the generated pulse waveform has a single first phase and a single second phase to generate a biphasic pulse waveform.

43. The method of claim 39, wherein the generated pulse waveform has the first phase that has a positive polarity and the second phase that has a negative polarity.

44. The method of claim 39, wherein the generated pulse waveform has the first phase that has a negative polarity and the second phase that has a positive polarity.

45. The method of claim 39, wherein the generated pulse waveform has an energy of between 0.1 to 200 joules of energy delivered to a patient during the first phase and second phase of the generated pulse waveform and an inter-pulse period between the first and second phases.

46. The method of claim 45, wherein the energy of the generated pulse waveform is delivered to the patient during a 2 ms to 20 ms time period.

47. The method of claim 39 further comprising adjusting a slope of at least one phase of the pulse waveform or an amplitude of at least one phase of the pulse waveform.

48. The method of claim 39 further comprising adjusting a timing for at least one phase of the pulse waveform.

49. The method of claim 48, wherein adjusting the timing for at least one phase of the pulse waveform further comprises taking a heart rhythm from a patient and adjusting the timing for at least one phase of the pulse waveform based on the heart rhythm of the patient.

50. The method of claim 39 further comprising adjusting a timing of an inter-phase period between the first phase and the second phase of the pulse waveform.

51. The method of claim 50, wherein adjusting the timing of the inter-phase period further comprises taking a heart rhythm from a patient and adjusting the timing of the inter-phase period based on the heart rhythm of the patient.

\* \* \* \* \*